US008088120B2

(12) United States Patent
Worsoff

(10) Patent No.: US 8,088,120 B2
(45) Date of Patent: Jan. 3, 2012

(54) METHOD AND APPARATUS FOR ALLEVIATING NASAL CONGESTION

(76) Inventor: Maya Worsoff, Toronto (CA)

(*) Notice: Subject to any disclaimer, the term of this patent is extended or adjusted under 35 U.S.C. 154(b) by 362 days.

(21) Appl. No.: 11/896,716

(22) Filed: Sep. 5, 2007

(65) Prior Publication Data

US 2009/0056709 A1    Mar. 5, 2009

(51) Int. Cl.
*A61M 31/00* (2006.01)
(52) U.S. Cl. ...................................... 604/514
(58) Field of Classification Search .............. 604/500, 604/514; 606/162; 128/898
See application file for complete search history.

(56) References Cited

U.S. PATENT DOCUMENTS

| 374,026 A | 11/1887 | Williams |
| 2,096,162 A | 10/1937 | Daley |
| 3,847,145 A * | 11/1974 | Grossan ........................ 601/160 |
| 5,496,338 A | 3/1996 | Miyagi et al. |
| 5,899,878 A | 5/1999 | Glassman |

OTHER PUBLICATIONS

"How to Induce". www.sneezefetishforum.org. Jun. 5, 2003. Accessed Jan. 11, 2010.*
Toshisada, Nishida; Nakamura, Miho. "Chimpanzee Tool Use to Clear a Blocked Nasal Passage." Folia Primatologica 1993; 61:218-220.*
Robert A. Freitas Jr., Nanomedicine, vol. IIA: Biocompatibility, Nanomedicine, vol. IIA: Biocompatibility, Landes Bioscience, Georgetown, TX, 2003.
Shin-Ichi Sekizawa, Teruhiko Ishikawa, and Giuseppe Sant'Ambrogio, Asymmetry in reflex responses of nasal muscles in anesthetized guinea pigs, Journal of Applied Physiology, Jul. 1998, pp. 123-128, vol. 85, Issue 1, Department of Physiology and Biophysics, The University of Texas Medical Branch, Galveston, Texas.
International Search Report issued by the International Searching Authority for International PCT Application No. PCT/CA2008/00160.

* cited by examiner

*Primary Examiner* — Nicholas Lucchesi
*Assistant Examiner* — Nathan R Price
(74) *Attorney, Agent, or Firm* — Fasken Martineau DuMoulin LLP

(57) ABSTRACT

The present invention relates generally to the field of treatments for nasal congestion, and in particular, to a method and apparatus for alleviating nasal congestion in a patient by mechanically stimulating the sneezing reflex in the patient to urge drainage of the nasal passageways. The method includes inserting an instrument having a work tip portion provided with at least one filament into the nostril of the patient. The nasal mucosa of the patient is then probed with the at least one filament to stimulate in the patient the sneeze reflex. This probing action causes the patient to sneeze. With the patient's mouth closed, the sneeze urges at least one of mucus, fluid and debris in the nasal passages of the patient to be forcibly expelled through the nostrils of the patient thereby draining the nasal cavity of the patient. The instrument used in the performance of this method includes a handle portion upon which the work tip portion is carried. The handle portion may be integrally formed with the work tip portion or releasably attachable thereto. The instrument is further provided with a physical stop associated with one of the work tip portion and the handle portion to prevent injury resulting from the working tip portion being inserted too deeply into the nasal passages of the patient.

13 Claims, 3 Drawing Sheets

METHOD AND APPARATUS FOR ALLEVIATING NASAL CONGESTION

FIELD OF THE INVENTION

The present invention relates generally to the field of treatments for nasal congestion, and in particular, to a method and apparatus for alleviating nasal congestion in a patient or user by mechanically stimulating the sneezing reflex in the patient to cause sneezing thereby encouraging drainage or clearing of mucus, fluids or the like from the patient's nasal or passages.

BACKGROUND OF THE INVENTION

Various methods of treatment and devices have been developed to alleviate nasal congestion. One such device is a nasal aspirator which utilizes vacuum pressure or suction to clear fluids, debris, mucus, secretions and the like from nasal and sinus passages. While such devices have been found to be generally effective, in some cases they have been found to cause discomfort, particularly in very young patients, for example, infants. Furthermore, the use of a nasal aspirator may not always be suitable to treat nasal congestion in infants because the application of a continuous suction force on the nasal passageways of the infant carries with it the risk that the fragile soft tissue of the nasal mucosa may be damaged during treatment. In light of the foregoing, it would be advantageous to have a device and method for treating and alleviating nasal congestion which avoids the above-mentioned drawbacks associated with the prior art. It would be further desirable if such a device was simply constructed and if such method of treatment were relatively easy to administer to a patient or to self-administer to oneself.

SUMMARY OF THE INVENTION

In accordance with one embodiment of the present invention, there is provided a method for alleviating nasal congestion in a patient. The method includes inserting an instrument having a work tip portion provided with at least one filament into the nostril of the patient. The nasal mucosa of the patient is probed with the at least one filament to stimulate in the patient the sneeze reflex. The method further includes causing the patient to sneeze with the patient's mouth closed to urge at least one of mucus, fluid and debris in the nasal passages of the patient to be forcibly expelled through the nostrils of the patient thereby draining the nasal cavity of the patient. In an additional feature, the method further includes clearing the patient's nasal passages of mucus and debris prior to inserting the instrument into the nostril of the patient.

In still another feature, the instrument includes a handle portion and the work tip portion is releasably attachable to the handle portion. The method further includes attaching the work tip portion to the handle portion prior to inserting the instrument into the nostril of the patient. Optionally, the method may include one of cleaning and sterilizing the work tip portion prior to inserting the instrument into the nostril of the patient. As a further option, the method may include moistening the at least one filament of the work tip portion prior to inserting the instrument into the nostril of the patient.

In yet another feature, the step of inserting includes inserting the instrument into the nostril of the patient with the patient's head inclined forward.

In additional feature, the method includes repeating the steps of inserting, probing and causing until such time as breathing through the nostril has improved and subsequently, drying out the patient's nasal passages by applying saline solution to the nasal mucosa of the patient.

In another feature, the nostril is a first nostril and the method further includes inserting the instrument into the second nostril of the patient; probing the nasal mucosa of the patient with the at least one filament to stimulate in the patient the sneeze reflex; and causing the patient to sneeze while maintaining the patient's mouth shut to urge at least one of mucus, fluid and debris in the nasal passages of the patient to be forcibly expelled through the nostrils of the patient thereby draining the nasal cavity of the patient.

In still another feature, the steps of inserting and probing are performed on the patient by a caregiver. Alternatively, the steps of inserting and probing are performed on the patient by the patient himself/herself. In one feature, the patient is human. In another feature, the patient is an animal.

In accordance with another embodiment of the present invention, there is provided an instrument for insertion into the nostril of a patient for probing the nasal mucosa of a patient to stimulate in the patient the sneeze reflex. The instrument has a handle portion for gripping the instrument and a work tip portion carried on the handle portion. The work tip portion has at least one filament. The instrument further includes a stop associated with one of the work tip portion and the handle portion. The stop is configured to limit insertion of the work tip portion into the nasal passages of the patient to thereby mitigate the risk of impalement injury.

In another feature, the work tip portion is integrally formed with the handle portion. Alternatively, the work tip portion may be releasably attached to the handle portion. In an additional feature, the work tip portion is intended for single use.

In yet another feature, the handle portion has a generally cylindrical body provided with a proximal end and a distal end. The work tip portion is mounted to the proximal end of the handle portion.

In still another feature, the at least one filament is mounted to extend substantially parallel to the longitudinal axis of the body.

In a further feature, the work tip portion includes a filament retaining portion to which is secured the at least one filament. In an additional feature, the at least one filament includes a plurality of filaments arranged in a tuft. The tuft is secured to the filament retaining portion.

In one feature, the at least one filament measures between about ¼ inch and 1½ inch, and more preferably, between about ½ inch and 1 inch. In another feature, the at least one filament is chosen from the group consisting of a synthetic fiber and a natural fiber. Where the at least one filament is a natural fiber, it may be human hair or animal hair.

In still another feature, the stop is provided on the work tip portion and integrally formed with the work tip portion. Additionally, the work tip portion includes a filament retaining portion to which is secured the at least one filament. The stop is defined by a flange projecting outwardly from the filament retaining portion. The flange is sized larger than the nostril of a patient.

In an alternative feature, the stop is provided on the handle portion and formed on the proximal end of the handle portion.

In accordance with still another embodiment of the present invention, there is provided an instrument for insertion into the nostril of a patient for probing the nasal mucosa of a patient to stimulate in the patient the sneeze reflex. The instrument has a handle portion for gripping the instrument and a work tip portion mountable on the handle portion. The work tip portion has at least one filament. The instrument further includes a stop associated with one of the work tip portion and the handle portion. The stop is configured to limit insertion of the work tip portion into the nasal passages of the patient to thereby mitigate the risk of impalement injury.

BRIEF DESCRIPTION OF THE DRAWINGS

The embodiments of the present invention shall be more clearly understood with reference to the following detailed description of the embodiments of the invention taken in conjunction with the accompanying drawings, in which.

DETAILED DESCRIPTION OF EMBODIMENTS OF THE INVENTION

Figure 1:
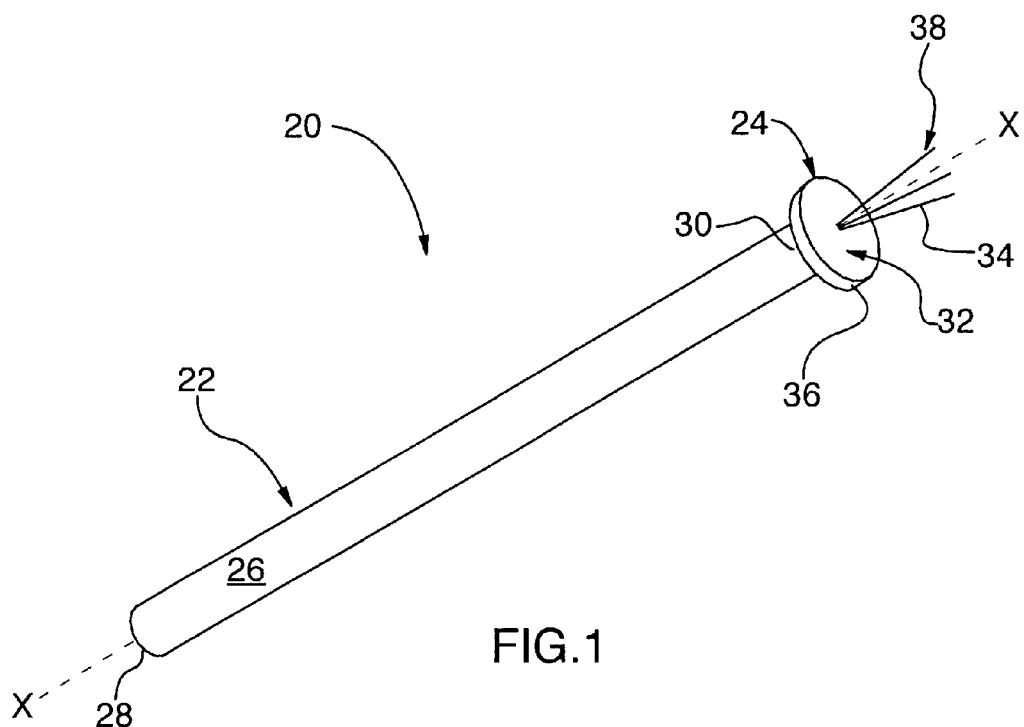
FIG. 1 is a perspective view of an instrument for mechanically stimulating the sneezing reflex in a patient or user, in accordance with an embodiment of the present invention.

The description, which follows, and the embodiments described therein are provided by way of illustration of an example, or examples of particular embodiments of principles and aspects of the present invention. These examples are provided for the purposes of explanation and not of limitation, of those principles of the invention. In the description that follows, like parts are marked throughout the specification and the drawings with the same respective reference numerals.

Figure 2:
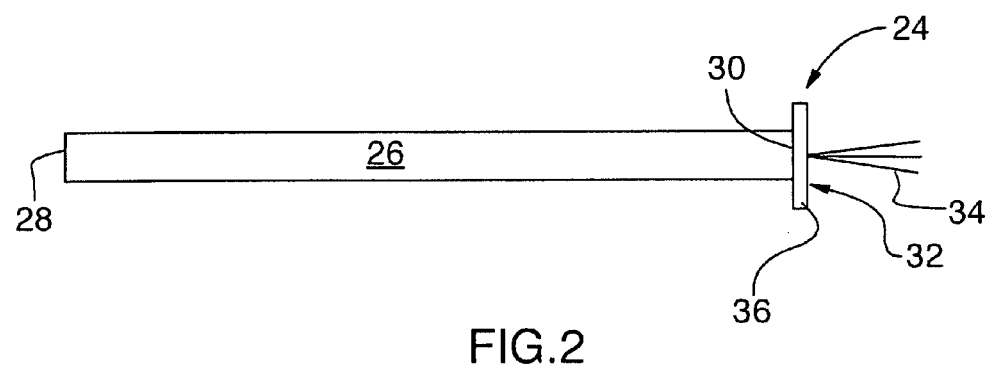
FIG. 2 is a side elevation view of the instrument shown in FIG. 1.

Referring to FIGS. 1 and 2, there is shown an instrument for mechanically stimulating or triggering the sneezing reflex in a patient or user, designated generally with reference numeral 20. The instrument 20 includes a handle portion 22 and a work tip portion 24 carried thereon. The handle portion 22 is configured to allow the instrument 20 to be easily gripped and manipulated during treatment. It has an elongate, generally cylindrical body 26 having a distal end 28 and a proximal end 30 upon which is mounted the work tip portion 24. The handle portion 22 may be made of plastic, rubber, stainless steel, or any other similar material. For reasons of cost and ease of manufacture, it is generally preferred that the handle portion be fabricated from rubber or plastic, particularly in instances where the instrument is intended to be disposable after a single use. Optionally, the handle portion may be provided with a textured surface, projections or rebates to enhance gripping of the instrument 20. Such surfaces or configurations could also be replaced with other grip enhancing means to similar advantage. For instance, the handle portion could have a hexagonal or octagonal cross-section.

Figure 3:
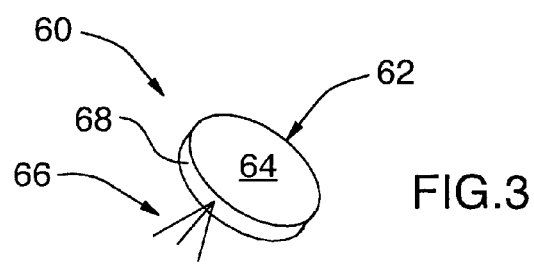
FIG. 3 is a perspective view of an alternate instrument to that shown in FIG. 1, in accordance with another embodiment of the present invention.

While in this embodiment, the body 26 of the handle portion 22 is stem-like, this need not be the case in every application. In other embodiments, the body of the handle portion 22 could be configured differently. With reference to FIG. 3, there is shown an alternate instrument designated generally with reference numeral 60. In this embodiment, the handle portion 62 is designed with a relatively small, disc-shaped body 64. Such a disc-shaped body 64 would be particularly well-adapted for being gripped between the index finger and thumb of a caregiver, patient or user. In this embodiment, a work tip portion 66 generally similar to work tip portion 24 is attached to the disc-shaped body 64 along a peripheral edge 68 thereof.

In the preferred embodiment, the work tip portion 24 is integrally formed with the handle portion 22 (i.e. of one-piece or unitary construction). However, this need not be the case in every application. In an alternative embodiment, these components may be manufactured separately from the same or different materials. Moreover, the work tip portion 24 may be configured for releasable attachment to the handle portion 22. This may be achieved in any number of ways. For example, the work tip portion 24 could have a threaded end, with corresponding threading provided on the proximal end 28 of the body 26. In this way, the threaded end of the work tip portion 24 could be threadingly fastened to the proximal end 28 for quick assembly. After use, the work tip portion 24 could be easily detached and replaced. Such a configuration is desirable in instances where the handle portion 24 is designed for reuse and where it is intended that the work tip portion 24 be disposed after a single use. By disposing of the work tip portion 24 after every use, the transmission of viruses, bacteria or diseases from one user or patient to another may be mitigated. Alternatively, releasable attachment of the work tip portion 24 to the handle portion 22 could be achieved by providing one of the proximal end 28 and the end opposite the work tip end 32 with a male portion and the other of the proximal end 28 and the opposite end of the work tip portion 32 with a female portion. In such an embodiment, the male and female portions of these components would be designed for mating with each other in a friction or interference fit.

The work tip portion 24 is adapted for insertion into the nostrils of a patient or user. It includes a filament retaining portion 32 and at least one hair-like filament, bristle or fibre 34 set in the filament retaining portion 32. The filament retaining portion 32 may be made from the same material as the handle portion 22. In the preferred embodiment, the filament retaining portion 32 is fabricated from plastic or rubber.

Extending outwardly from the filament retaining portion 32 is a generally circular flange 36 which is sized larger than the nostril 42 of the patient to be treated 44. In this arrangement, the flange 36 functions as a physical stop for preventing the caregiver or user 40 from inserting the working tip portion 24 too deeply into the nasal passages 56 of the patient 44. In addition, this flange further protects the patient 44 from an impalement injury arising from the instrument 20 being thrust violently into the patient's nasal cavity 52 during a sneeze.

While in this embodiment, the flange 36 has a circular shape, it will be appreciated that in other embodiments, the flange could be shaped differently. In still other embodiments, the flange may be replaced with one or more alternate structures which could perform the stop function. Accordingly, the width, diameter or shape of the filament retaining portion 32 may be appropriately sized to serve this function. For example, the filament retaining portion may be formed with a bulbous shape whose widest dimension is sized larger than the diameter of a typical patient's nostril 42.

Further modifications are also possible. For example, while in the embodiment shown, the stop is integrally formed with the filament retaining portion, in other embodiments, the stop could be a separate component detachable from the filament retaining portion. Moreover, while in the preferred embodiment, the stop is provided on the work tip portion, in alternative embodiments, it may be associated with the handle portion. In such embodiments, the stop could be formed on the proximal end of the handle portion body.

The working tip portion 24 has more than one filament 34, and more preferably, three filaments, arranged in a tuft 38. The tuft 38 can be secured into the filament retaining portion 32 in a number of different ways. For instance, the filaments 34 of the tuft 38 may be stapled or anchored to the filament retaining portion 32 using known techniques, such as those used in the manufacture of toothbrushes. Alternatively, the filaments 34 may be fused to the filament retaining portion 32.

In the embodiment shown, the filaments 34 are mounted to extend substantially parallel to the longitudinal axis X-X of the body 26. In other embodiments, the filaments could be oriented differently relative to the longitudinal axis X-X of the body 26. For instance, the filaments could be mounted perpendicular to the longitudinal axis X-X of the body 26. By configuring the instrument 20 in this fashion, it may be possible to further reduce the risk of impalement injury to the patient 44 during treatment.

Preferably, each filament 34 measures between about ¼ inch and 1.5 inches and more preferably, between about ½ inch and 1 inch. It is further preferred that the filament 34 be relatively soft, but possess some stiffness. The length of the filaments may be adjusted to suit the size of the patient 44 or the user. For instance, where the patient to be treated is in an infant, it may be desirable to use a shorter length of filament than in the case where the patient or user is an adult, so as to prevent the filaments from being inserted too deeply into the patient's nasal passageways. The filaments 34 are preferably, hypoallergenic and may be synthetic, for example, extruded nylon filament, or natural fibers, preferably soft hair in the nature of human or animal hair.

Figure 4:
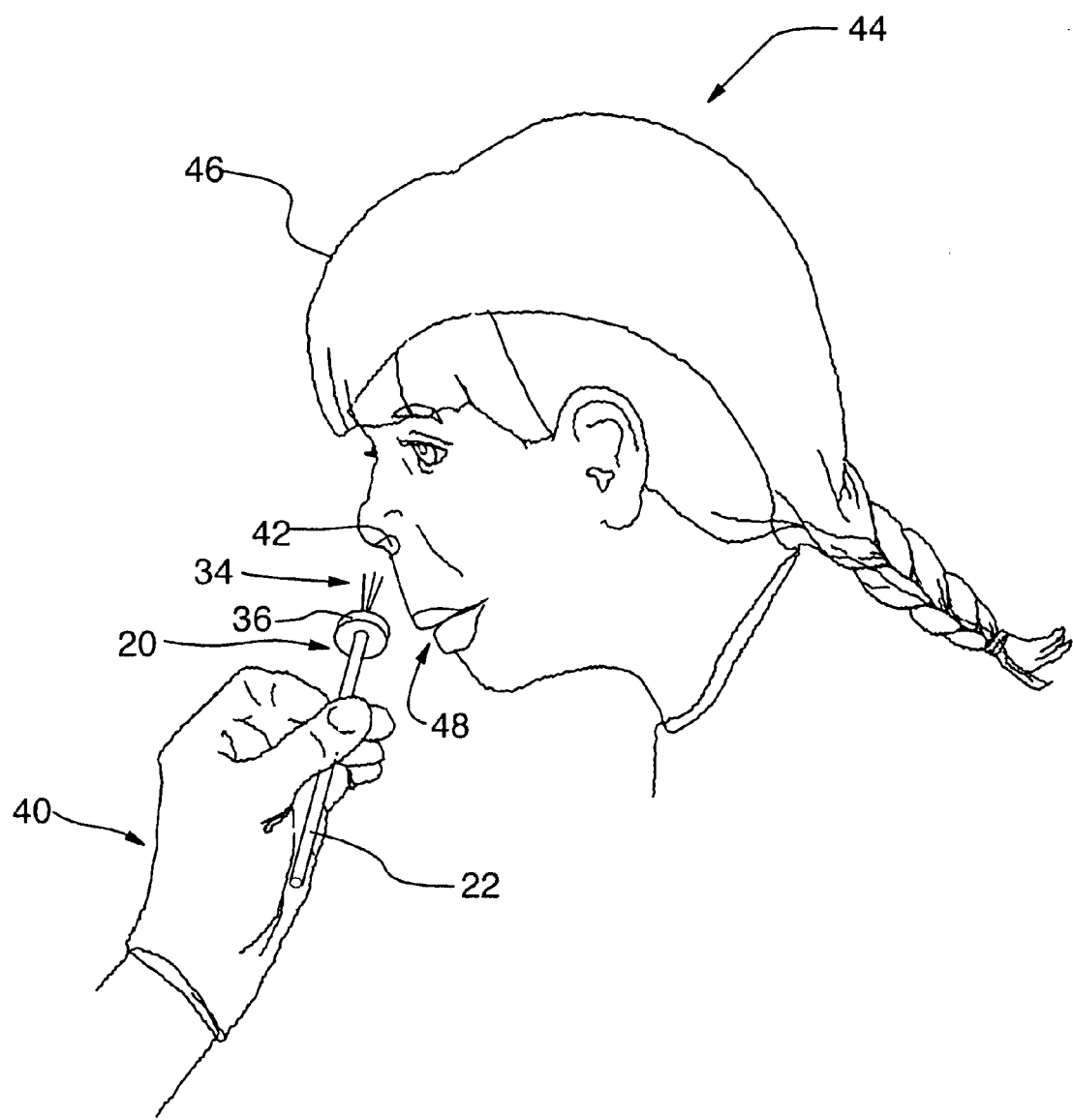
FIG. 4 is a schematic drawing showing a caregiver administering to a patient a treatment for alleviating nasal congestion, in accordance with an embodiment of the present invention.
Figure 5:
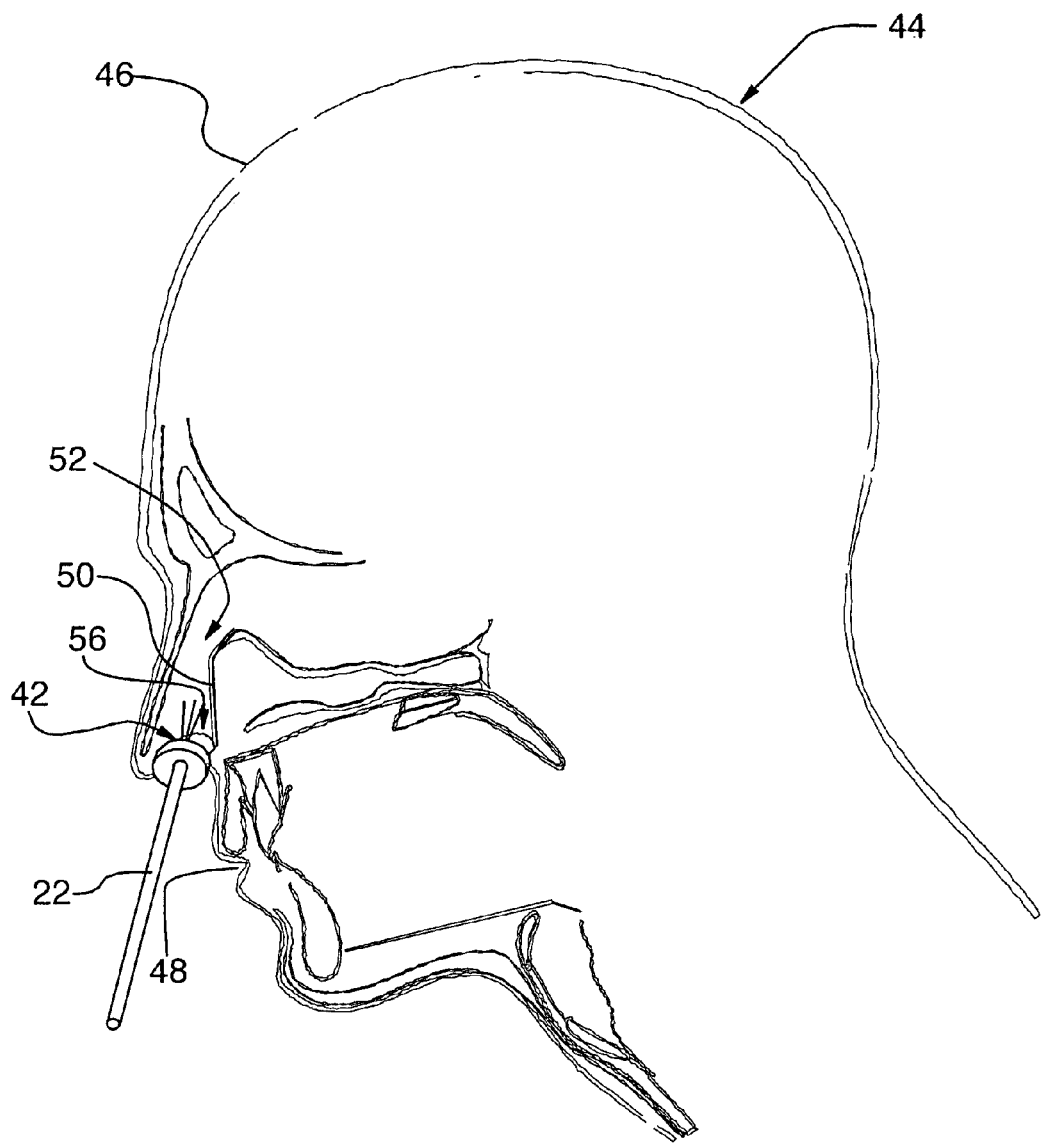
FIG. 5 is a simplified cross-sectional view of the patient shown in FIG. 4 illustrating the instrument inserted in the nostril of the patient.

An exemplary method of treatment using the instrument 20 is now described in greater detail with reference to FIGS. 4 and 5. To begin a caregiver 40 grips the handle portion 22 of the instrument 20. If the instrument 20 is of the type having a disposable work tip portion 24, the caregiver 40 attaches a new work tip portion 24 to the handle portion 22. Alternatively, if the work tip portion 24 is designed for repeated use, the caregiver 40 ensures that the filaments 34 are clean and/or sterilized prior to administering the treatment. Accordingly, the caregiver may wash or disinfect the filaments 34.

Next, the caregiver ensures that the nasal passages are relatively dry and free of obstruction (that is, relatively clear of mucus or debris) which could otherwise interfere with the insertion of the instrument 20 in the nostril of the patient 44. If the nostrils are obstructed or if there is continual nasal drip, the caregiver will attempt to clear the nasal passages 56 with a cotton swab. Once the nostrils are cleared of mucus, fluid and debris and are relatively dry, the caregiver will administer the treatment to the patient.

The caregiver 40 inserts the working tip portion 34 into the first nostril 42 of the patient 44 (in this case a young girl shown in FIG. 4) while ensuring that the patient's head 46 is bent slightly forward. Optionally, prior to inserting the working tip portion 34 into patient's nostril, the caregiver 40 may moisten the filaments 34 to increase the stiffness thereof. The caregiver 40 then gently probes either side of the nasal mucosa 50 with the filaments 34 to trigger the patient's sneezing reflex. After sufficient stimulation, the patient 44 will tend to sneeze. Care is taken to ensure that the patient's mouth 48 is completely shut during the sneeze. Because the patient's head 46 is bent forwardly and her mouth 44 is kept shut, the sudden pressure caused by the sneeze tends to urge the mucus and fluids which create the congestion in the nasal cavity 52 to be forcibly expelled through the nostrils 42 and 54 of the patient 44, thereby draining or clearing the nasal cavity 52. These steps may be repeated several times until breathing through that nostril 42 has improved and a relatively clear watery fluid begins to drain from the first nostril 42. At that time, a cotton swab whose tip has been imbibed with a saline solution is inserted into the first nostril 42 and urged to contact the nasal mucosa 50. The application of the saline solution on the nasal mucosa 50 tends to reduce or dry up the remaining nasal drip. With the congestion cleared from the first nostril 42, the operation is then repeated on the second nostril (not shown) of the patient 44.

While an exemplary method has been described with reference to a caregiver 40 administering treatment on a patient 44, it should be appreciated that the treatment could also be self-administered by a user on himself/herself.

Furthermore, while the foregoing method may be successfully used to alleviate nasal congestion in humans, it should be appreciated that this method may also be used to similar advantage in the treatment of nasal congestion in animals.

Although the foregoing description and accompanying drawings relate to specific preferred embodiments of the present invention as presently contemplated by the inventor, it will be understood that various changes, modifications and adaptations, may be made without departing from the spirit of the invention.

What is claimed is:

1. A method for alleviating nasal congestion in a patient, the method comprising:
   providing an instrument for insertion into the nostril of a patient for probing the nasal mucosa of a patient, the instrument having:
      a handle portion for gripping the instrument;
      a work tip portion carried on the handle portion, the work tip portion provided with a tuft of bristles; and
      a stop associated with one of the work tip portion and the handle portion, the stop being configured to limit insertion of the work tip portion into the nasal passages of the patient to thereby mitigate the risk of impalement injury;
   while the head of the patient is bent forward, inserting the tuft of bristles into the nostril of the patient no further than the stop;
   probing the nasal mucosa of the patient with the at least one filament to stimulate in the patient the sneeze reflex; and
   causing the patient to sneeze with the patient's mouth closed to urge at least one of mucus, fluid and debris in the nasal passages of the patient to be forcibly expelled through the nostrils of the patient thereby draining the nasal cavity of the patient.

2. The method of claim 1 further including clearing the patient's nasal passages of mucus and debris prior to inserting the tuft of bristles into the nostril of the patient.

3. The method of claim 1 wherein:
   the work tip portion is releasably attachable to the handle portion; and
   the method further includes attaching the work tip portion to the handle portion prior to inserting the tuft of bristles into the nostril of the patient.

4. The method of claim 1 further including one of cleaning and sterilizing the tuft of bristles portion prior to inserting the tuft of bristles into the nostril of the patient.

5. The method of claim 1 further including moistening the tuft of bristles of the work tip portion prior to inserting the tuft of bristles into the nostril of the patient.

6. The method of claim 1 wherein further including repeating the steps of inserting, probing and causing until such time as breathing through the nostril has improved.

7. The method of claim 6 further including drying out the patient's nasal passages after performing the repeating step.

8. The method of claim 7 wherein the step of drying includes applying saline solution to the nasal mucosa of the patient.

9. The method of claim 1 wherein:
   the nostril is a first nostril; and
   the method further includes:
   inserting the tuft of bristles into the second nostril of the patient;
   probing the nasal mucosa of the patient with the tuft of bristles to stimulate in the patient the sneeze reflex; and
   causing the patient to sneeze while maintaining the patient's mouth shut to urge at least one of mucus, fluid and debris in the nasal passages of the patient to be forcibly expelled through the nostrils of the patient thereby draining the nasal cavity of the patient.

10. The method of claim 1 wherein the steps of inserting and probing are performed on the patient by a caregiver.

11. The method of claim 1 wherein the steps of inserting and probing are performed on the patient by the patient himself/herself.

12. The method of claim 1 wherein the patient is human.

13. The method of claim 1 wherein the patient is an animal.

* * * * *